(12) United States Patent
Hill

(10) Patent No.: US 7,052,473 B2
(45) Date of Patent: May 30, 2006

(54) BODY INSERT CONFIGURING DEVICE HAVING TIP PORTION WITH EXPANDABLE JOINTS

(75) Inventor: Rolf Hill, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 632 days.

(21) Appl. No.: 10/311,566

(22) PCT Filed: Jun. 19, 2001

(86) PCT No.: PCT/SE01/01423

§ 371 (c)(1),
(2), (4) Date: Dec. 16, 2002

(87) PCT Pub. No.: WO02/00287

PCT Pub. Date: Jan. 3, 2002

(65) Prior Publication Data

US 2003/0139793 A1    Jul. 24, 2003

(30) Foreign Application Priority Data

Jun. 30, 2000 (SE) .................................... 0002515

(51) Int. Cl.
*A61M 25/01* (2006.01)
(52) U.S. Cl. ...................... 600/585; 600/151; 606/129; 606/108; 128/899
(58) Field of Classification Search ................ 600/585, 600/141, 143, 146, 151; 607/116, 122, 125; 128/899; 606/108, 129
See application file for complete search history.

(56) References Cited

U.S. PATENT DOCUMENTS 4,758,222 A    7/1988  McCoy
5,211,183 A    5/1993  Wilson
5,228,441 A *  7/1993  Lundquist .................... 600/380

(Continued)

FOREIGN PATENT DOCUMENTS

EP         0 773 037        5/1997
WO      WO 00/22981        4/2000

OTHER PUBLICATIONS

"New Small Radius Joints Based on Thermal Shrinkage of Polyimide in V-grooves fro Robust Self-Assembly 3D Microstructures," Ebefors et al., J. Microtech. Microeng., vol. 8 (1998) pp. 188-194.

(Continued)

*Primary Examiner*—Kennedy Schaetzle
(74) *Attorney, Agent, or Firm*—Schiff Hardin LLP

(57) ABSTRACT

A device for configuring a body insert, such as an electrode lead for a stimulation device, has a wire arrangement adapted to be inserted into the interior of the body insert for stiffening and bending the body insert. The wire arrangement has a tip section which, when the wire arrangement is inserted in the body insert, resides at the distal end thereof. The tip section has a bendable insulating polymer element which contains a number of bending actuators connected in series. The bending actuators are formed by successive silicon sections interconnected by polyimide-filled V-groove joints in thermal communication with a heating element. The operation of the heating element from a regulation unit adapted for access at a proximal end of the body insert controls expansion of the polyimide filling the joints, thereby producing a selected amount of bending at the tip section and the distal end section of the body insert.

8 Claims, 1 Drawing Sheet

U.S. PATENT DOCUMENTS

| | | |
|---|---|---|
| 5,279,559 A | 1/1994 | Barr |
| 5,415,633 A | 5/1995 | Lazarus et al. |
| 5,624,380 A * | 4/1997 | Takayama et al. .......... 600/146 |
| 6,245,444 B1 * | 6/2001 | Marcus et al. .............. 428/616 |
| 6,907,298 B1 * | 6/2005 | Smits et al. ................ 607/125 |

OTHER PUBLICATIONS

"Dynamic Actuation Of Polyimide V-Groove Joints By Electrical Heating", Ebefors et al., Sensors and Actuators, vol. A-67 (1998) pp. 199-204.

* cited by examiner

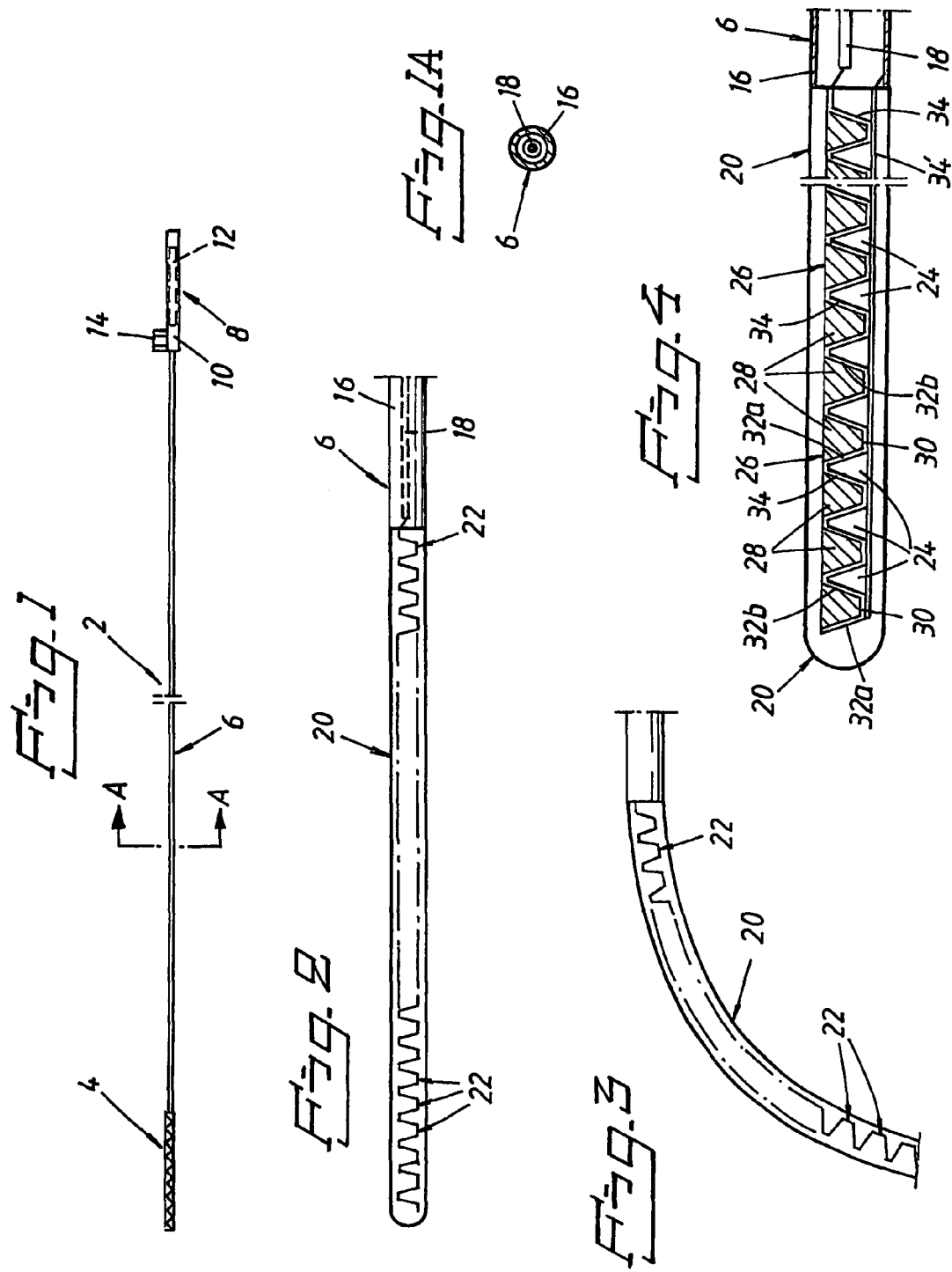

BODY INSERT CONFIGURING DEVICE HAVING TIP PORTION WITH EXPANDABLE JOINTS

BACKGROUND OF THE INVENTION

1. Field of the Invention

The present invention relates to an electrically controlled configuring device having a tip section provided at a distal end of a wire arrangement and a regulation unit provided at a proximal end of the wire arrangement, the device being adapted to be inserted into an interior channel within an elongated flexible component to stiffen that component and bend a distal end section thereof into a required shape.

An elongated flexible component of the aforementioned kind may be e.g. a hollow electrode cable used for stimulation in the human body, e.g. an electrode cable or pacing lead for a heart stimulator. Such electrode cable may be devised to serve either as an implant or for removal from the human body after a medical treatment has been performed.

2. Description of the Prior Art

A standard type of body insert configuring device generally in use today is a stylet unit (or mandrin) used for stiffening and guiding an electrode cable (pacing lead) for a heart stimulator or pacemaker during insertion, advancing and positioning of such a cable or lead into a human heart, and when the contact electrode at or near the distal tip end of the cable is to be anchored in a cavity of the heart. Such a temporarily introduced stylet unit inside the electrode cable or pacing lead extends through the cable's interior channel from the proximal end of the cable to the distal end thereof where the contact electrode is mounted.

This kind of stylet unit normally has a flexible, tubular stylet shell containing a stylet wire longitudinally movable within the shell's interior channel.

To prevent the stylet wire from rotating in relation to its surrounding tubular stylet shell (sleeve) it is preferred to use a shell (sleeve) with an interior channel having a non-circular cross-section in combination with a stylet wire having a corresponding non-circular cross-section. European Application 0 773 037 A2 describes a guide wire unit where the stylet wire is prevented from rotating in its surrounding shell (sleeve) by means of interacting non-circular cross-sections.

When a pacing lead contact electrode is to be positioned and anchored in the heart's atrium using a stylet unit, it is required that an appropriate J-shape be imparted to the distal end or tip section of the pacing lead, by means of the stylet unit. A suitable J-shape will highly facilitate the insertion of the distal end section of the pacing lead into the atrial auricle as well as the anchoring of the contact electrode in the trabeculae of the atrial auricle.

After the pacing lead contact electrode has become duly positioned and anchored at the desired site in the heart, the stylet unit is withdrawn completely from the interior channel of the pacing lead and thereby from the heart.

The above kind of stylet unit is relatively difficult to manufacture and furthermore is dependent on free longitudinal movement between the two parts and it would be desirable to have a configuring device that is not dependent on relative longitudinal movement between different parts.

U.S. Pat. No. 4,758,222 discloses a device having an electrically controlled catheter. The catheter incorporates parts made of memory metal that will change from one state to another when subjected to heating. The memory metal parts are heated by means of electrical current supplied from a power unit via longitudinal conducting means. When the memory metal parts are heated, the catheter will be deflected.

U.S. Pat. No. 5,211,183 discloses a guidewire for access to a body structure or location by inserting it into the body and advancing it to the desired location. The guide wire includes shape memory means that may be heated by means of induction heating, immersion heating, application of RF energy or by body heating, the guide wire thus being deflected when heated.

Neither of the two above devices is designed for use in an internal lumen in for instance an endocardial pacing electrode lead or the like. Both also are limited to discrete changes in shape in view of the nature of shape-memory materials.

SUMMARY OF THE INVENTION

A primary object of the present invention is to provide a configuring device which may be used for bending at least a portion or section of a tubular elongated flexible component without utilizing any longitudinal movement between interacting, mutually displaceable elements, by providing an electrically controlled locating device having a tip section which can be bent into a J-shaped configuration. The locating device further should be easy and cheap to manufacture and it should be possible to manufacture very thin locating devices.

According to the invention these when designing a configuring device may be attained by utilizing the principles for thermally expansive joints for microactuators as described in 1) Ebefors et al, "New small radius joints based on thermal shrinkage of polyimides in V-grooves for robust self-assembly 3D microstructures", J. Micromech.—Microeng. 8 (1998) 188–194, IOP Publishing Ltd 1998, and 2) Ebefors et al "Dynamic actuation of polyimide V-groove joints by electrical heating", Sensors and Actuators A 67 (1998) 199–204, Elsevier Science S.A. 1998, both articles hereby being incorporated by reference.

In configuring device according to the invention the tip section includes a bendable insulating polymer element containing a sequence of bending actuators. In this sequence the bending actuators are connected after each other, i.e. in series. Each bending actuator is formed of silicon plate sections interconnected by polyimide filled V-groove joints which are provided with a heating element allowing the bending angles of the V-groove joints to be controlled by thermal expansion of the cured polyimide fillings of the V-grooves. As indicated in the above articles a useful polyimide is Selectilux® HTR-3200 from OCG.

The dynamic and reversible thermal expansion of the cured polyimide fillings is preferably done by electricity, more precisely by regulating an electric current supplied to the heating element which may be formed by resistive heaters integrated with the polyimide fillings. A temperature increase in the joints will result in an expansion of the polyimide and thereby a dynamic change of the bending angles of the V-groove joints. If the V-grooves are defined by metal foil wall portions, for instance made of aluminum, these wall portions may constitute the resistive heaters used for producing the local heat dissipation in the joints.

A dynamic bending angle of at least 3°–4° per V-groove is certainly possible with this type of design. Consequently, a series of 45–60 bending actuators will be sufficient for obtaining an accumulated 180° bending angle corresponding to a desirable U- or J-shaped total bending angle.

The individual bending actuator may have two or more silicon plate sections interconnected by polyimide filled V-groove joints. The V-groove defining surfaces of the V-groove joints may be lined with layers of electrically conductive material, e.g. aluminum, constituting integrated heating means in the form of resistors on the wall surfaces of the V-grooves.

Furthermore, according to the present invention the wire arrangement may have a flexible, tubular stylet shell and a single lead wire inside the longitudinal interior channel of the shell. The regulation unit (at the proximal end of said wire arrangement) preferably has a manipulator housing containing a power source (e.g. an electric battery) connected to the wire arrangement. The regulation unit may be provided with an adjustable potentiometer for controlling the intensity of the current supplied to the heating element.

As indicated in the above articles, the wire arrangement will be easy to manufacture by bulk micro-machining methods for silicon substrates which after the completed manufacturing process easily can be cut into long strips. It is thus also possible to manufacture a very thin wire arrangement. Since the deflection is dependent on heat expansion instead on shape memory, the deflection will be continuous.

DESCRIPTION OF THE DRAWINGS

FIG. 1 very schematically shows a configuring device in accordance with the invention.

FIG. 1A shows (on a larger scale) a cross section of the wire arrangement, at line A—A in FIG. 1.

FIG. 2 shows the bendable tip section of the locating device, in a straight not yet bent state.

FIG. 3 shows the bendable tip section in a bent state.

FIG. 4 shows, in longitudinal section, very schematically and on a distorted scale, the fundamental construction of a bendable tip section containing a number of interconnected bending actuators.

DESCRIPTION OF THE PREFERRED EMBODIMENTS

In FIG. 1 there is shown in side elevation an elongated configuring device 2 adapted to be used e.g. for stiffening and guiding a tubular bendable pacing lead (not shown), which is connected to a heart stimulator (not shown), when such pacing lead is to be inserted, advanced and positioned in a human body so that a tip electrode at the distal end of the lead becomes suitably positioned and can be anchored in a cavity of the heart. The elongated configuring device 2 has a bendable tip section 4 arranged at the distal end of a tubular wire arrangement 6 and is provided at its proximal end with a handle-like regulation unit 8. The unit 8 has a manipulator housing 10 containing an electric battery 12 and is provided at the forward end thereof with an adjustable potentiometer 14 used for controlling the electric current supply from the battery 12 via the wire arrangement 6 to an electric heating element within the bendable tip section 4.

In the present case the wire arrangement 6 preferably comprises a relatively stiff, thin metal tube 16 containing in its interior channel an insulated single-core line wire 18 (see enlarged cross-section of FIG. 1A). The tube 16, which preferably is made of stainless steel, itself will constitute the first pole, and the line wire 18 the second pole, of the bipolar wire arrangement 6. The outer diameter of the tube 16 may be e.g. 0.4 mm, and the inner diameter thereof may be about 0.3 mm.

A preferred type and structure of the bendable tip section 4 of the configuring device 2 will now be described more in detail and with reference to FIGS. 2–4.

The bendable tip section 4 has a bendable insulating casing 20 made of a suitable polymer. This outer polymer casing 20 contains a number of bending actuators 22 being connected in series to be able to provide, together, a reversible, accumulated 180° bending angle corresponding to a contemplated U- or J-shape. Each bending actuator is formed by two silicon plates or beam sections 24 interconnected by an intermediate polyimide filled V-groove joint 26. The polyimide filling in each such joint is constituted by a cured polyimide body 28 positioned in a support channel (defining the V-groove) formed by a bottom portion 30 and a pair of opposite flanks 32a, 32b being integral parts of a cross corrugated metal foil strip 34. The V-groove angle between the flanks 32a, 32b constitutes a dynamic and reversible "bending angle" the magnitude of which can be changed by controlling the thermal expansion of the cured polyimide body 28. In this case the metal foil strip 34 is used as a resistive heater producing local heat dissipation (temperature increase) in the polyimide body of the joint 26. A temperature increase in the polyimide body 28 will result in an expansion of the polyimide, thereby providing a dynamic change of the bending angle. Large bending angles can be obtained by connecting a number of V-groove joints 26 in series.

The under side (as seen in the drawing) of the bendable tip section is provided with a second conducting layer 34' separated from the bendable tip by means of an insulating layer. This conducting layer is connected to the metal tube 16.

Instead of using the metal foil strip 34 as a resistive heater for controlling the expansion of the polyimide bodies 28, it is possible to use some other type of heating element, e.g. an electric heating element fully integrated (embedded or contained) in the polyimide bodies 28. Regardless of the type of heating element used for controlling the bending angles of the series of interconnected V-groove joints 26 it is only required to have the heating element connected to a pair of electric wires (or pole means) for supplying the current necessary to produce the local heat dissipation in the joints.

In the description above, the metal tube 16 has been illustrated as being the second conductor in the above device. It should however be noted that this part of the stylet unit could be designed at will as long as there are two conducting paths for the electrical current to be supplied to the bendable tip.

The initial shape of the wire can be determined by means of the curing of the polyimide since the polyimide shrinks when cured.

Although modifications and changes may be suggested by those skilled in the art, it is the invention of the inventor to embody within the patent warranted heron all changes and modifications as reasonably and properly come within the scope of his contribution to the art.

I claim as my invention:

1. A device adapted for insertion in an interior channel of an elongated, flexible body insert having a distal end portion and a proximal end portion, for stiffening said insert and for bending said distal end portion thereof, said device comprising:

a wire arrangement adapted for insertion in said channel, having a tip end adapted to reside at said distal end section when said wire arrangement is inserted in said channel;

said tip section comprising a bendable, insulating polymer element and a sequence of bending actuators formed by a plurality of silicon sections interconnected by polyimide-filled V-groove joints, and a heating element in thermal communication with said polyimide-filled V-groove joints, said heating element causing bending of said joints and configuring of said tip section by thermal expansion of said polyimide; and a manipulable regulation unit adapted to be accessible at said proximal end of said insert, connected to said wire arrangement.

2. A device as claimed in claim 1 wherein each bending actuator comprises at least three silicon sections interconnected by two polyimide-filled V-groove joints.

3. A device as claimed in claim 1 wherein said sequence of bending actuators, in combination, produces a bend in said tip section of approximately 180°, forming said tip section into a J-shaped configuration.

4. A device as claimed in claim 1 wherein said heating element comprises an electrical heating element integrated in said V-groove joints.

5. A device as claimed in claim 4 wherein each of said V-groove joints has a V-groove surface and comprising layers of electrically conductive material lining each V-groove surface forming a resistor in each of said V-groove joints, the respective resistors in said V-groove joints forming said integrated heating element.

6. A device as claimed in claim 5 wherein said layers are comprised of aluminum.

7. A device as claimed in claim 5 comprising a pair of electrical wires proceeding along said V-groove joints forming said integrated heating element said wires being adapted for connection to a power supply for dissipating heat into said V-groove joints.

8. A device as claimed in claim 1 wherein said wire arrangement comprises a flexible, tubular stylet jacket having a longitudinal channel therein, and a single lead wire proceeding through said longitudinal channel, and wherein said regulation unit comprises a manipulator housing containing a power source connected to said heating element and a potentiometer for controlling said power source for controlling heating of said V-groove joints by said heating element.

* * * * *